(12) United States Patent
Hirahara et al.

(10) Patent No.: US 9,138,399 B2
(45) Date of Patent: Sep. 22, 2015

(54) CLEANING AGENT COMPOSITION

(75) Inventors: Mayuko Hirahara, Bunkyo-ku (JP); Izumi Katsuta, Bunkyo-ku (JP)

(73) Assignee: KAO CORPORATION, Tokyo (JP)

(*) Notice: Subject to any disclaimer, the term of this patent is extended or adjusted under 35 U.S.C. 154(b) by 3 days.

(21) Appl. No.: 14/115,193

(22) PCT Filed: May 1, 2012

(86) PCT No.: PCT/JP2012/061555
§ 371 (c)(1),
(2), (4) Date: Nov. 1, 2013

(87) PCT Pub. No.: WO2012/150711
PCT Pub. Date: Nov. 8, 2012

(65) Prior Publication Data
US 2014/0130822 A1    May 15, 2014

(30) Foreign Application Priority Data

May 2, 2011 (JP) .................. 2011-103055

(51) Int. Cl.
| A61Q 19/10 | (2006.01) |
| A61K 8/73 | (2006.01) |
| A61K 8/39 | (2006.01) |
| A61K 8/37 | (2006.01) |
| C08B 11/193 | (2006.01) |
| C08L 1/26 | (2006.01) |
| C08L 1/28 | (2006.01) |
| C08B 1/06 | (2006.01) |
| C08B 1/08 | (2006.01) |
| C08B 11/08 | (2006.01) |
| C08B 11/145 | (2006.01) |
| C08B 11/20 | (2006.01) |

(52) U.S. Cl.
CPC . *A61K 8/731* (2013.01); *A61K 8/37* (2013.01); *A61K 8/39* (2013.01); *A61K 8/73* (2013.01); *A61Q 19/10* (2013.01); *C08B 1/06* (2013.01); *C08B 1/08* (2013.01); *C08B 11/08* (2013.01); *C08B 11/145* (2013.01); *C08B 11/193* (2013.01); *C08B 11/20* (2013.01); *C08L 1/26* (2013.01); *C08L 1/284* (2013.01); *C08L 1/288* (2013.01)

(58) Field of Classification Search
None
See application file for complete search history.

(56) References Cited

U.S. PATENT DOCUMENTS

| 3,472,840 | A | 10/1969 | Stone et al. | |
| 3,816,616 | A | 6/1974 | Anguillo et al. | |
| 4,759,875 | A | 7/1988 | Hart | |
| 7,960,327 | B2 * | 6/2011 | Uchiyama et al. | 510/130 |
| 2010/0038585 | A1 * | 2/2010 | Hosoya et al. | 252/182.12 |
| 2010/0274001 | A1 | 10/2010 | Okutsu et al. | |
| 2012/0230934 | A1 | 9/2012 | Doi et al. | |
| 2013/0149276 | A1 | 6/2013 | Takeuchi et al. | |
| 2013/0296212 | A1 | 11/2013 | Fujii et al. | |

FOREIGN PATENT DOCUMENTS

| CN | 102596166 A | 7/2012 |
| EP | 2 500 012 A1 | 9/2012 |
| EP | 2 659 878 A1 | 11/2013 |
| GB | 2219594 | * 12/1989 |
| JP | 45 20318 | 7/1970 |
| JP | 59 42681 | 10/1984 |
| JP | 62 190298 | 8/1987 |
| JP | 5-112795 A | 5/1993 |
| JP | 11-35432 A | 2/1999 |
| JP | 11-263715 A | 9/1999 |
| JP | 2000-319139 A | 11/2000 |
| JP | 2001-172166 A | 6/2001 |

(Continued)

OTHER PUBLICATIONS

Extended Search Report issued on Nov. 6, 2014 in European Patent Application No. 12779823.9.
U.S. Appl. No. 14/114,544, filed Oct. 29, 2013, Hirahara, et al.
U.S. Appl. No. 14/115,521, filed Nov. 4, 2014, Hirahara, et al.
International Preliminary Report on Patentability and Written Opinion issued Nov. 14, 2013 in Application No. PCT/JP2012/061555 (English Translation).

(Continued)

*Primary Examiner* — Jyothsna Venkat
(74) *Attorney, Agent, or Firm* — Oblon, McClelland, Maier & Neustadt, L.L.P.

(57) ABSTRACT

A cleansing composition comprising the following components (A), (B), and (C):
(A) from 1 to 20% by weight of a polyoxyethylene alkyl ether carboxylate in which the average addition mole number of the polyoxyethylene is 3.5 or less and the number of carbons in the alkyl group is from 10 to 18,
(B) from 0.02 to 10% by weight of cationized hydroxypropyl cellulose represented by the following formula (1), wherein $R^1$, $R^2$ and $R^3$ each independently represent a substituent group having a cationized ethyleneoxy group and a propyleneoxy group, n represents a number of from 20 to 5000 which is a number representing the average polymerization degree of anhydroglucose, and the substitution degree of the cationized ethyleneoxy group is from 0.01 to 3 and the substitution degree of the propyleneoxy group is from 0.01 to 5, and
(C) water.

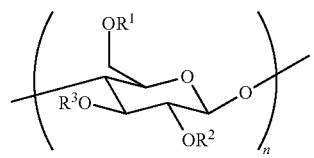

(1)

15 Claims, No Drawings

(56) References Cited

FOREIGN PATENT DOCUMENTS

| | | |
|---|---|---|
| JP | 2005 239616 | 9/2005 |
| JP | 2005 306843 | 11/2005 |
| JP | 2009 143997 | 7/2009 |
| JP | 2009-263291 | 11/2009 |
| JP | 2010-70529 A | 4/2010 |
| JP | 2010-138075 A | 6/2010 |
| JP | 2010-138083 A | 6/2010 |
| WO | WO 2008004342 * | 1/2008 |
| WO | 2011 059063 | 5/2011 |
| WO | 2012 091072 | 7/2012 |

OTHER PUBLICATIONS

International Search Report Issued Aug. 14, 2012 in PCT/JP12/061555 Filed May 1, 2012.

"New Cosmetics Studies" Nanzando, Second Edition, Jan. 18, 2001, pp. 441-445 with unedited computer generated English translation.

* cited by examiner

CLEANING AGENT COMPOSITION

FIELD OF THE INVENTION

The present invention relates to a cleansing composition.

BACKGROUND OF THE INVENTION

Among various performances required for skin cleansing compositions for cleansing the face and body, mild cleansing performance, quick disappearance of slimy feel and a feel with frictional resistance (stop feeling) are important as a feel to the touch during rinsing after cleansing. Allowing the slimy feel to more quickly disappear in the course of rinsing and allowing the skin to have stronger sense of stop feeling are more preferred, because a refreshed clean feeling can be obtained.

Conventionally, a skin cleansing composition containing a polyoxyethylene alkyl ether sulfate, which is a commonly used surfactant, as a main ingredient has been well known in the present field of art. Although the polyoxyethylene alkyl ether sulfate has good lathering ability, it is problematic in that slimy feel is persistently present during the course of rinsing. Patent Document 1 discloses a composition in which a polyoxyethylene alkyl ether sulfate and a fatty ether carboxylate surfactant are used in combination, which shows mild cleansing performance and good lathering ability. However, it also shows strong slimy feel during rinsing, and thus refreshing cleansing feel cannot be obtained and also moist skin feel cannot be obtained after cleansing. Thus, it was not found to be completely satisfactory.

In Patent Document 2, a cleansing composition containing a specific surfactant and a cationic polymer is disclosed. In a hair cleanser, the cationic polymer is used as a conditioning agent for reducing a frictional feeling, and improves finger combing during rinsing. In a skin cleansing agent, it is also used as a conditioning agent to moisturize the skin.

CITATION LIST

Patent Document

Patent Document 1: Japanese Patent Application Laid-Open (JP-A) No. 62-190298
Patent Document 2: JP-A-2005-306843

SUMMARY OF THE INVENTION

The present invention is to provide a cleansing composition comprising the following components (A), (B), and (C):

(A) from 1 to 20% by weight of a polyoxyethylene alkyl ether carboxylate in which the average addition mole number of the polyoxyethylene is 3.5 or less and the number of carbons in the alkyl group is from 10 to 18, (B) from 0.02 to 10% by weight of cationized hydroxypropyl cellulose represented by the following formula (1),

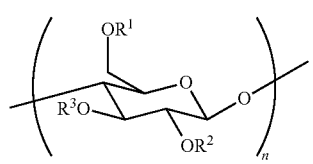

wherein $R^1$, $R^2$ and $R^3$ each independently represent a substituent group having a cationized ethyleneoxy group and a propyleneoxy group represented by the following formula (2) or (3), n represents a number of from 20 to 5000 which is a number representing the average polymerization degree of anhydroglucose, and the substitution degree of the cationized ethyleneoxy group is from 0.01 to 3 and the substitution degree of the propyleneoxy group is from 0.01 to 5,

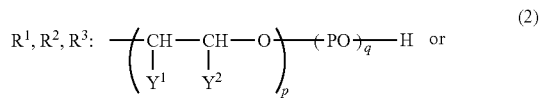

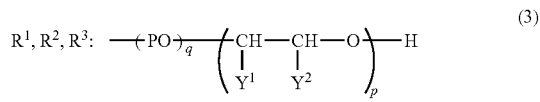

wherein one of $Y^1$ and $Y^2$ represents a hydrogen atom and the other is a cationic group represented by the following formula (4), PO represents a propyleneoxy group, p represents the number of the cationized ethyleneoxy group ($-CH(Y^1)-CH(Y^2)-O-$) in the formula (2) or (3), q represents the number of the propyleneoxy group ($-PO-$) in the formula (2) or (3), each representing 0 or a positive number, in which, when none of p and q is 0, the cationized ethyleneoxy group and the propyleneoxy group may be added in any order, and when at least one selected from p and q is 2 or higher, it may be any one of a block bond or a random bond,

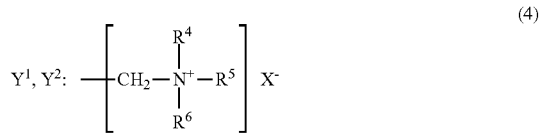

wherein $R^4$, $R^5$ and $R^6$ each independently represent a linear or branched alkyl group having from 1 to 3 carbon atoms, and $X^-$ represents an anionic group, and (C) water.

DESCRIPTION OF EMBODIMENTS

In the intended use of skin cleansing, conventional cleansing compositions are not completely satisfactory in that there are causes for slimy feel which persists for a long period of time and a stop feeling property is hardly expressed during rinsing.

The present invention relates to a cleansing composition which exhibits excellent foam quality and excellent cleansing feel during cleansing, has a strong stop feeling property due to quick disappearance of slimy feel during rinsing, and provides an excellent moist feeling of the skin after drying.

The inventors of the present invention found that, by combining a specific polyoxyethylene alkyl ether carboxylate with a specific cationized polymer, a cleansing composition which can solve the problems described above can be provided.

The cleansing composition of the invention gives creamy foam and excellent cleansing feel during cleansing, quick disappearance of slimy feel during rinsing, excellent stop feeling during rinsing, and moist skin feel after drying. In addition, the skin immediately after towel dried can be given with moist feeling like the hands adsorbing onto the skin.

As for the polyoxyethylene alkyl ether carboxylate used as the component (A) in the present invention, those represented by the following formula in which the average addition mole number of the polyoxyethylene is 3.5 or less and the number of carbons in the alkyl group is from 10 to 18 are preferable.

R—O(CH$_2$CH$_2$O)$_n$CH$_2$—COOX wherein R represents an alkyl group or an alkenyl group having from 10 to 18 carbon atoms, n represents a number of from 0.5 to 3.5 on average, and X represents a hydrogen atom, an alkali metal, an alkali earth metal, ammonium or organic ammonium.

In the formula, an alkyl group having from 12 to 16 carbon atoms may be preferred as R. A mixture having from 12 and 14 carbon atoms is more preferable. In addition, the average addition mole number of ethylene oxide is preferably in the range from 0.5 to 3.5, more preferably from 1 to 2.9, and even more preferably 2.6.

Further, as X, an alkali metal such as sodium or potassium; an alkali earth metal such as calcium or magnesium; ammonium; an ammonium derived from an alkanolamine such as monoethanolamine, diethanolamine or triethanolamine; a cation derived from a basic amino acid such as arginine or lysine, and the like may be mentioned. Among them, from the viewpoint of less coloration of the composition, an alkali metal salt and ammonium salt are preferable. An alkali metal salt is more preferable.

One or two or more types of the component (A) may be used. From the viewpoint of having less change in viscosity according to temperature change so that foam volume and foam quality can be maintained without having rough dry skin after cleansing, it may be contained, as a salt in the total composition, at 1% by weight or more, preferably 1.5% by weight or more, and more preferably 2% by weight or more. Further, the upper limit is 20% by weight or less, preferably 11% by weight or less, and more preferably 6% by weight or less. Taken together the above aspects, as a salt in the total composition, it is contained at from 1 to 20% by weight, preferably from 1 to 11% by weight, and more preferably from 1.5 to 6% by weight.

The component (B) used in the present invention is cationized hydroxypropyl cellulose represented by the above formula (1), in which a main chain derived from anhydroglucose is contained, the substitution degree of the cationized ethyleneoxy group is from 0.01 to 3, and the substitution degree of the propyleneoxy group is from 0.01 to 5 (hereinafter, also referred to as "C—HPC").

(Main Chain Derived from Anhydroglucose Represented by the Formula (1))

The main chain derived from anhydroglucose which is represented by the formula (1) has a main chain derived from anhydroglucose, as shown in the above formula (1).

In the formula (1), $R^1$, $R^2$ and $R^3$ each independently represent a substituent group represented by the formula (2) or (3), in which $R^1$, $R^2$ and $R^3$ may be the same or different from each other. In addition, each of $R^1$ in the number of n, $R^2$ in the number of n, and $R^3$ in the number of n may be the same or different from each other.

From the viewpoint of having a stop feeling property during rinsing after cleansing with the cleansing composition of the present invention and good smoothness accompanied with moist feeling of skin after drying, the average polymerization degree n in the formula (1) is 20 or higher, preferably 100 or higher, and more preferably 400 or higher. Further, the upper limit is 5000 or lower, preferably 2000 or lower, and more preferably 1300 or lower. Taken together the above aspects, the average polymerization degree n in the formula (1) is from 20 to 5000, preferably from 100 to 2000, and more preferably from 400 to 1300.

Meanwhile, as described herein, the average polymerization degree indicates viscosity average polymerization degree that is measured by copper-ammonia method, and it is specifically calculated by the method described in Examples.

(Substituent Group Represented by the Formula (2) or (3))

In the formula (1), the substitution group represented by the formula (2) or (3) as $R^1$, $R^2$, or $R^3$ has, as shown in the above formula (2) or (3), a cationized ethyleneoxy group and a propyleneoxy group.

In the formula (2) or (3), one of $Y^1$ and $Y^2$ is a hydrogen atom and the other is a cationic group represented by the formula (3), and PO represents a propyleneoxy group.

p represents the number of the cationized ethyleneoxy group (—CH($Y^1$)—CH($Y^2$)—O—) in the formula (2) or (3), and it is 0 or a positive number. From the viewpoint of ease of production, p is preferably 0 or 1.

q represents the number of the propyleneoxy group (—PO—) in the formula (2) or (3), and it is 0 or a positive number. From the viewpoint of ease of production, q is preferably a number of from 0 to 4, more preferably a number of from 0 to 2, and even more preferably 0 or 1.

When various substituent groups represented by the formula (2) or (3) are present in a C—HPC molecule, each of p and q may be different among the substituent groups.

From the viewpoint of ease y production, the sum of p and q is preferably a number of from 1 to 5, more preferably a number of from 1 to 4, even more preferably a number of from 1 to 3, and further even more preferably 1 or 2.

When none of p and q is 0, the cationized ethyleneoxy group and the propyleneoxy group may be added in any order. However, from the viewpoint of production efficiency, it is preferably an order described in the formula (3).

In addition, when none of p and q is 0 and at least one selected from p and q is 2 or higher, it is sufficient to have any one of a block bond and a random bond. However, from the viewpoint of ease of production, it is preferably a block bond.

In at least one of $R^1$ in the number of n, $R^2$ in the number of n, and $R^3$ in the number of n, p in the formula (2) or (3) is not 0, and in at least one of them, q in the formula (2) or (3) is not 0.

(Cationic Group Represented by the Formula (4))

In the formula (2) or (3), the cationic group represented by the formula (4) as $Y^1$ and $Y^2$ has a structure represented by the above formula (4).

$R^4$, $R^5$ and $R^6$ in the formula (4) each independently represent a linear or branched alkyl group having 1 to 3 carbon atoms, and specific examples thereof include a methyl group, an ethyl group, a n-propyl group and an isopropyl group. Among them, from the viewpoint of water solubility of C—HPC, a methyl group and an ethyl group are preferable, and a methyl group is more preferable.

In the formula (4), $X^-$ represents an anionic group as a counter ion of the ammonium group. $X^-$ is not limited, if it is an anionic group. Specific examples thereof include alkyl sulfate ions, sulfate ions, phosphate ions, alkyl carbonate ions, and halide ions. Among them, from the viewpoint of ease of production, halide ions are preferable. Examples of the halide ions include fluoride ions, chloride ions, bromide ions, and iodide ions. From the viewpoint of water solubility and chemical stability of C—HPC, chloride ions and bromide ions are preferable, and chloride ions are more preferable.

In C—HPC represented by the formula (1), from the viewpoint of enhancing lathering during cleansing, having strong feel with frictional resistance (that is, stop feeling property)

by quickly removing slimy feel during rinsing after cleansing, and obtaining a good feel accompanying moistness after the skin is dried, the substitution degree of the cationized ethyleneoxy group is preferably from 0.01 to 3, more preferably from 0.1 to 2.4, and even more preferably from 0.18 to 1.

According to the present invention, the substitution degree of the cationized ethyleneoxy group means the average mole number of the cationized ethyleneoxy group that is present in C—HPC molecule per mole of anhydroglucose unit constituting the cellulose main chain. The substitution degree of the cationized ethyleneoxy group is measured according to the method described in the following Examples.

Further, from the viewpoint of degree of foamability during cleansing, foam dissipation during rinsing, and having foam removing property, the substitution degree of the propyleneoxy group is from 0.01 to 5, preferably from 0.2 to 3, and more preferably from 1.1 to 2.9.

According to the present invention, the substitution degree of the propyleneoxy group means the average mole number of the propyleneoxy group that is present in C—HPC molecule per mole of anhydroglucose unit constituting the cellulose main chain. The substitution degree of the propyleneoxy group is measured according to the method described in the following Examples.

C—HPC of the component (C) can be obtained by the following production methods (1) to (3), for example.

(1) A method in which cellulose, water in a large amount, and alkali metal hydroxide in an excess amount are mixed in slurry form, and reacted with a cationizing agent and propylene oxide.

(2) A method in which dimethyl acetamide containing lithium chloride is used as a solvent and cellulose is dissolved by adding amines or an alcoholate catalyst, followed by reaction with a cationizing agent and propylene oxide.

(3) A method in which without using water in an excess amount or a solvent like the above (1) and (2), cellulose in powder, pellet, or chip state, a cationizing agent, and propylene oxide are reacted with one another in the presence of a base.

According to the above production methods (1) to (3), the reaction with a cationizing agent and the reaction with propylene oxide may be carried out in any order or may be carried out simultaneously.

Among the above production methods, from the viewpoint of ease of production, the production method (3) is preferable.

One or two or more types of C—HPC may be used as the component (B). From the viewpoint of strength of a stop feeling property during rinsing and having moist skin feel after drying, it is contained at 0.02% by weight or more, preferably 0.2% by weight or more, and more preferably 0.4% by weight or more in the total composition. In addition, it is 10% by weight or less, preferably 2% by weight or less, and more preferably 1% by weight or less in the total composition. Taken together the above aspects, it is contained in an amount of from 0.02 to 10% by weight, preferably from 0.2 to 2% by weight, and more preferably from 0.4 to 1% by weight in the entire composition.

According to the present invention, the weight ratio between the components (A) and (B), that is, (B)/(A), is preferably from 0.01 to 2, from the viewpoint of having foam quality after cleansing, reduction of slimy feel during rinsing, having stop feeling at certain strength, and imparting moistness like the hands adsorbing onto the skin immediately after cleansing and towel blotting and a natural moist feeling to the skin after drying. More preferably, it is from 0.03 to 1, and even more preferably from 0.07 to 0.5.

Water as the component (C) constitutes balance of each component, and it is preferably contained in an amount of from 40 to 95% by weight in the total composition.

The cleansing composition according to the present invention may further comprise, as the component (D), an anionic surfactant other than the component (A). The anionic surfactant as the component (D) may increase foam volume during cleansing and lower slimy feel during rinsing so that stop feeling can be increased to high level.

The anionic surfactant used as the component (D) in the present invention is not specifically limited if it is commonly used for a cleansing composition. Examples thereof include alkyl sulfate, polyoxyalkylene alkyl ether sulfate, polyoxyalkylene alkenyl ether sulfate, sulfosuccinic acid alkyl ester salt, polyoxyalkylene sulfosuccinic acid alkyl ester salt, α-olefin sulfonate, fatty acid salt, N-acylamino acid salt, N-acylalkyl taurine salt, and the like.

Among them, from the viewpoint of foamability or cleansing ability, polyoxyalkylene alkyl ether sulfate, fatty acid salt, N-acylamino acid salt, and N-acylalkyl taurine salt are preferable, and polyoxyalkylene alkyl ether sulfate and fatty acid salt are more preferable.

Further, examples of the salt as the component (D) include a salt of an alkali metal salt such as sodium and potassium; a salt of an alkali earth metal such as calcium and magnesium; an ammonium salt; a salt of alkanolamine such as monoethanol amine, diethanol amine, and triethanol amine; and a salt of basic amino acid such as arginine and lysine, and the like. Among them, from the viewpoint of less coloration of the composition, a salt of an alkali metal and an ammonium salt are preferable. A salt of an alkali metal is more preferable.

As the component (D), one or two or more types may be used. When used, it is contained at 1% by weight or more, preferably 2% by weight or more, and more preferably 3% by weight or more, and at 30% by weight or less, preferably 15% by weight or less, and more preferably 12% by weight or less as a salt in the total composition from the viewpoint of having excellent lathering ability and foam increasing ability and enhancing stop feeling by combination of the components (A) and (B). Taken together the above aspects, it is preferably contained in an amount of from 1 to 30% by weight, more preferably from 2 to 15% by weight, and even more preferably from 3 to 12% by weight as a salt in the total composition.

The cleansing composition according to the present invention may further comprise (E) a salt. The salt is preferably an inorganic salt or an organic acid salt having 6 or less carbon atoms.

Examples of the inorganic salt include salts between alkali metals or alkali earth metals and halogens, sulfuric acid, sulfurous acid, phosphoric acid and the like. Specific examples thereof include sodium chloride, potassium chloride, sodium bromide, magnesium chloride, sodium sulfate, potassium sulfate, sodium dihydrogen phosphate, disodium hydrogen phosphate, and the like. Examples of the organic acid salt include salts between acetic acid, or hydroxy acids or polyacids such as lactic acid, malic acid, citric acid and succinic acid, and alkali metals or the like.

Among them, preferred are sodium chloride, sodium malate, sodium lactate, sodium citrate, and sodium succinate.

As the component (E), one or two or more types may be used within the range not interfering the foamability or foam quality as effects of the present invention. When used, the component (E) is preferably contained in an amount of from 0.1 to 6% by weight and preferably from 0.5 to 3% by weight in the total composition. When it is within the above range, the dissolution of the complex formed of the components (A)

and (B) or the components (A), (B), and (D) is facilitated so that the complex in dissolution state can be contained in a large amount. Further, precipitation amount of the complex can be increased during the rinsing process, and therefore desirable. As a result, the stop feeling property is improved, and thus a strong stop feeling property can be obtained.

According to the present invention, when the component (E) is contained, the weight ratio among the components (A), (B), (D), and (E), (E)/((A)+(B)+(D)), is preferably 0.02 or more and more preferably 0.1 or more, and preferably 0.4 or less and more preferably 0.3 or less from the viewpoint of providing flexible resilience to dry skin after cleansing. Taken together the above aspects, it is preferably from 0.02 to 0.4 and more preferably from 0.1 to 0.3.

According to the present invention, (F) long chain fatty acid glycol ester represented by the following formula may be also comprised in the composition.

wherein $R^{11}$ represents an alkyl group or an alkenyl group having from 11 to 21 carbon atoms, A represents a hydrogen atom or $COR^{12}$ ($R^{12}$ represents an alkyl group or an alkenyl group having from 11 to 21 carbon atoms, and m represents a number of from 1 to 3.

The long chain fatty acid glycol ester is present as flake-like crystal in the cleansing composition of the present invention.

Further, during the rinsing process after cleansing, the long chain fatty acid glycol ester is adsorbed onto skin with the complex formed of the components (A) and (B) or the components (A), (B), and (D), and it can induce moist feeling after drying.

When the component (F) is contained in the composition, from the viewpoint of skin feeling after cleansing, the component (F) is preferably contained at 0.5% by weight or more and more preferably 1% by weight or more and preferably 3% by weight or less, more preferably 2.5% by weight or less, and even more preferably 2% by weight or less in the total composition. Taken together the above aspects, it is preferably contained in an amount of from 0.5 to 3% by weight, and more preferably from 1 to 2.5% by weight in the total composition.

The cleansing composition of the present invention may also comprise (G) at least one selected from an alkyl polyglycoside-based non-ionic surfactant and a polyoxyethylene alkyl ether-based non-ionic surfactant. They can yield high foam volume during cleansing.

Alkyl polyglycosides are a non-ionic surfactant derived from sugars and higher alcohols, and examples thereof include those represented by the following formula.

wherein R represents an alkyl group having 9 to 20 carbon atoms, m represents, on average, a number of from 0 to 10, Z represents a sugar residue having 5 or 6 carbon atoms, and x represents, on average, a number of from 1 to 5.

In the formula, R is preferably an alkyl group having 9 to 15 carbon atoms, and it may be a mixture of them. Z is preferably pentose or hexose, and among them, glucose is more preferable. m is, on average, preferably a number of from 0 to 5, and x is, on average, a number of from 1 to 3.

As the polyoxyethylene alkyl ether-based non-ionic surfactant, those having an alkyl group with 12 to 22 carbon atoms, and those having an addition mole number of polyoxyethylene group of from 10 to 30 are preferable. Specific examples thereof include polyoxyethylene lauryl ether, polyoxyethylene myristyl ether, polyoxyethylene palmityl ether, polyoxyethylene isostearyl ether, polyoxyethylene stearyl ether, polyoxyethylene oleyl ether, polyoxyethylene hexyldecyl ether, polyoxyethylene octyldodecyl ether, polyoxyethylene behenyl ether, and the like.

Further, polyoxyethylene alkyl ether-based non-ionic surfactants having HLB of from 10 to 20, and also having HLB of from 13 to 16 are more preferable because a cleansing composition having more excellent transparency can be obtained.

Meanwhile, HLB is an index indicating a balance between hydrophilicity and hydrophobicity (Hydropile Balance), and in the present invention, the values calculated according to the following equation by Oda and Teramura et al are used.

$$HLB = \frac{\Sigma \text{ Inorganic value}}{\Sigma \text{ Organic value}} \times 10$$

Examples of the polyoxyethylene alkyl ether-based non-ionic surfactant include polyoxyethylene (21) lauryl ether (EMULGEN 121-G (HLB 14), manufactured by Kao Corporation), polyoxyethylene (20) 2-hexyldecyl ether (EMULGEN 1620G (HLB 14), manufactured by Kao Corporation), polyoxyethylene (20) octyl dodecyl ether (EMULGEN 2020G (HLB 13), manufactured by Kao Corporation), polyoxyethylene (16) lauryl ether (EMULGEN 116 (HLB 15.8), manufactured by Kao Corporation), and the like.

As for the component (G), from the viewpoint of having an excellent skin feel of towel-dried skin after cleansing, alkyl polyglycoside is preferable.

One or two or more types of the component (G) may be used. When it is contained, from the viewpoint of having foam volume of the cleansing composition and a feel to the touch during rinsing, it is preferably contained in an amount of 0.05% by weight or more, more preferably 0.2% by weight or more, and even more preferably 0.5% by weight or more in the total composition. Further, it is preferably contained in an amount of 10% by weight or less, more preferably 6% by weight or less, and even more preferably 4% by weight or less in the total composition. Taken together the above aspects, it is preferably contained in an amount of from 0.05 to 10% by weight, more preferably from 0.2 to 6% by weight, and even more preferably from 0.5 to 4% by weight in the total composition.

The cleansing composition of the present invention may also comprise (H) amphoteric surfactant.

Examples of the amphoteric surfactant as the component (H) include carbobetaine, sulfobetaine, imidazolium betaine, amide betaine, and the like, and by using it, the lathering ability can be further improved without suppressing rinsing property. Specific examples thereof include fatty acid amide propylbetaine, alkyl hydroxy sulfobetaine, and the like.

One or two or more types of the component (H) may be used. When it is contained, the component (H) is preferably contained in an amount of 0.1% by weight or more and more preferably 0.5% by weight or more in the total composition. Further, it is preferably contained in an amount of 10% by weight or less and more preferably 6% by weight or less in the total composition. Taken together the above aspects, it is preferably contained in an amount of from 0.1 to 10% by weight, and also from 0.5 to 6% by weight in the total composition, from the viewpoint of improving foamability.

The cleansing composition of the present invention may also comprise polyol, and as a result, the moisture retaining property of skin can be further improved.

The polyol is a polyhydric alcohol having two or more hydroxy groups in the molecule, and specific examples thereof include alkylene glycol such as ethylene glycol, propylene glycol, 1,3-butylene glycol, and 1,4-butylene glycol; polyalkylene glycol such as dipropylene glycol; sugar alcohols such as glucose, maltose, maltitose, sucrose, fructose, xylitol, sorbitol, maltotriose, and threitol; glycerin, polyglycerin, erythritol, alcohol obtained by degradation and reduction of starch, and the like.

One or two or more types of polyol may be used. When it is contained, it is preferably contained in an amount of from 0.1 to 40% by weight, more preferably from 1 to 20% by weight, and even more preferably from 3 to 10% by weight in the total composition.

The cleansing composition of the present invention may also comprise components used in ordinary cleansing composition, for example, an oily component, an anti-bacterial agent, an anti-inflammatory agent, a preservative, a chelating agent, a scrubbing agent, a fragrance, a cooling agent, a pigment, an UV absorbing agent, an antioxidant, plant extract, and the like.

The cleansing composition of the present invention may be produced by adding each component in order in water and dissolving them by fully stirring at from 20 to 70° C. When a powder polymer is mixed, it is preferable that the polymer be first dispersed in water and then each component be mixed with each other.

The cleansing composition of the present invention preferably has pH of from 5 to 10, and more preferably pH of from 5.7 to 9.1 at 30° C.

In the present invention, pH is measured after diluted 20 times by weight with water.

The cleansing composition of the present invention may be applied to a skin cleansing agent such as hand soap, hand wash, facial wash, cleansing foam, and body cleansing agent such as body soap, and also a hair cleansing agent such as shampoo. It is also preferred as a skin cleansing agent for body.

The method for cleansing skin by using the cleansing composition of the present invention is as follows. Specifically, the cleansing composition of the present invention is applied in an appropriate amount to a body, that is, a body skin part such as face, hand or feet, and torso, allowed to generate foams for cleansing, and rinsed off using hot water by shower, or the like. It is also possible that a suitable amount is added onto a cleansing aid tool such as towel, sponge, and brush and allowed to generate foams for cleansing.

With regard to the embodiments described above, the invention also discloses the following composition, method, and use.

<1> A cleansing composition comprising the following components (A), (B), and (C):

(A) from 1 to 20% by weight of a polyoxyethylene alkyl ether carboxylate in which the average addition mole number of the polyoxyethylene is 3.5 or less and the number of carbons in the alkyl group is from 10 to 18, (B) from 0.02 to 10% by weight of cationized hydroxypropyl cellulose represented by the following formula (1),

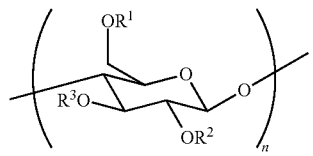

(1)

wherein $R^1$, $R^2$, and $R^3$ each independently represent a substituent group having a cationized ethyleneoxy group and a propyleneoxy group represented by the formula (2) or (3), n represents a number of from 20 to 5000 which is a number representing the average polymerization degree of anhydroglucose, and the substitution degree of the cationized ethyleneoxy group is from 0.01 to 3 and the substitution degree of the propyleneoxy group is from 0.01 to 5,

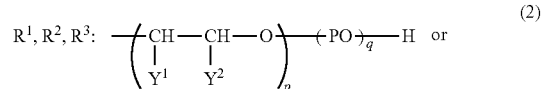

(2)

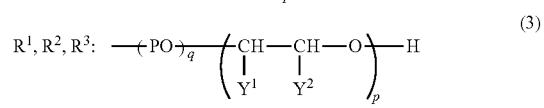

(3)

wherein one of $Y^1$ and $Y^2$ represents a hydrogen atom and the other is a cationic group represented by the following formula (4), PO represents a propyleneoxy group, p represents the number of the cationized ethyleneoxy group (—CH($Y^1$)—CH($Y^2$)—O—) in the formula (2) or (3), q represents the number of the propyleneoxy group (—PO—) in the formula (2) or (3), each representing 0 or a positive number, in which, when none of p and q is 0, the cationized ethyleneoxy group and propyleneoxy group may be added in any order, and when at least one selected from p and q is 2 or higher, it may be any one of a block bond or a random bond,

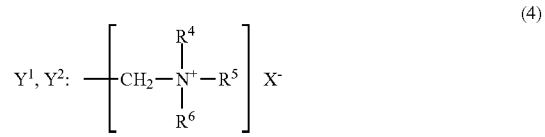

(4)

wherein $R^4$, $R^5$, and $R^6$ each independently represent a linear or branched alkyl group having from 1 to 3 carbon atoms, and $X^-$ represents an anionic group, and (C) water.

<2> The cleansing composition described in above <1>, further comprising (D) an anionic surfactant other than the component (A).

<3> The cleansing composition described in above <1> or <2>, further comprising (E) a salt.

<4> The cleansing composition described in any one of above <1> to <3>, further comprising (F) a long chain fatty acid glycol ester represented by the following formula:

$$R^{11}COO(CH_2CH_2O)_mA$$

wherein $R^{11}$ represents an alkyl group or an alkenyl group having from 11 to 21 carbon atoms, A represents a hydrogen atom or $COR^{12}$ in which $R^{12}$ represents an alkyl group or an alkenyl group having from 11 to 21 carbon atoms, and m represents a number of from 1 to 3.

<5> The cleansing composition described in any one of above <1> to <4>, further comprising at least one non-ionic surfactant selected from (G) an alkyl polyglycoside-based non-ionic surfactant and a polyoxyethylene alkyl ether-based non-ionic surfactant.

<6> The cleansing composition described in any one of above <1> to <5>, in which the weight ratio between the components (A) and (B), (B)/(A), is from 0.01 to 2, preferably from 0.03 to 1, and more preferably from 0.07 to 0.5.

<7> The cleansing composition described in any one of above <3> to <6>, in which the weight ratio between the components (A), (B), (D), and (E), (E)/((A)+(B)+(D)), is 0.02 or more and preferably 0.1 or more, and 0.4 or less and preferably 0.3 or less.

<8> The cleansing composition described in any one of above <1> to <7>, in which the average addition mole number of the polyoxyethylene is 3.5 or less, preferably from 0.5 to 3.5, and more preferably from 1 to 2.9, and even more preferably 2.6, and the alkyl group has carbon atom number of from 10 to 18, preferably from 12 to 16, and may be a mixture of carbon atom number of 12 and 14 in polyoxyethylene alkyl ether carboxylate as the component (A).

<9> The cleansing composition described in any one of above <1> to <8>, in which, for the component (B), the average polymerization degree n in the formula (1) is 20 or higher, preferably 100 or higher, and more preferably 400 or higher, and 5000 or lower, preferably 2000 or lower, and more preferably 1300 or lower, the substitution degree of the cationized ethyleneoxy group is 0.01 or higher, preferably 0.1 or higher, and more preferably 0.18 or higher, and 3 or lower, preferably 2.4 or lower, and more preferably 1 or lower, and the substitution degree of the propyleneoxy group is 0.01 or higher, preferably 0.2 or higher, and more preferably 1.1, and 5 or less, preferably 3 or less, and more preferably 2.9 or less.

<10> The cleansing composition described in any one of above <2> to <9>, in which the anionic surfactant as the component (D) is at least one selected from polyoxyalkylene alkyl ether sulfate, fatty acid salt, N-acylamino acid salt, and N-acylalkyl taurine salt, preferably polyoxyalkylene alkyl ether sulfate or fatty acid salt.

<11> The cleansing composition described in any one of above <3> to <10>, in which the salt as the component (E) is an inorganic salt or an organic acid salt having 6 carbon atoms or less, and preferably at least one selected from sodium chloride, sodium malate, sodium lactate, sodium citrate, and sodium succinate.

<12> The cleansing composition described in any one of above <4> to <11>, in which the component (F) is a long chain fatty acid glycol ester represented by the following formula:

$$R^{11}COO(CH_2CH_2O)_mA$$

wherein $R^{11}$ represents an alkyl group or an alkenyl group having from 11 to 21 carbon atoms, A represents a hydrogen atom or $COR^{12}$ in which $R^{12}$ represents an alkyl group or an alkenyl group having from 11 to 21 carbon atoms, and m represents a number of from 1 to 3.

<13> The cleansing composition described in any one of above <5> to <12>, in which the component (G) has HLB of from 10 to 20, and preferably HLB of from 13 to 16.

<14> The cleansing composition described in any one of above <5> to <13>, in which, in the component (G), the alkyl polyglycoside-based non-ionic surfactant is at least one selected from alkyl (C10-16) polyglucoside and alkyl (C9-11) glucoside and the polyoxyethylene alkyl ether-based surfactant is at least one selected from polyoxyethylene (21) lauryl ether (HLB 14), polyoxyethylene (20) 2-hexyldecyl ether (HLB 14), polyoxyethylene (20) octyl dodecyl ether (HLB 13), and polyoxyethylene (16) lauryl ether (HLB 15.8), and preferably polyoxyethylene (16) lauryl ether.

<15> The cleansing composition described in any one of above <1> to <14>, in which the content of the component (A) is 1% by weight or more, and preferably 1.5% by weight or more, and 20% by weight or less, preferably 11% by weight or less, and more preferably 6% by weight or less in the total composition.

<16> The cleansing composition described in any one of above <1> to <15>, in which the content of the component (B) is 0.02% by weight or more, preferably 0.2% by weight or more, and more preferably 0.4% by weight or more, and 10% by weight or less, and preferably 2% by weight or less, and more preferably 1% by weight or less in the total composition.

<17> The cleansing composition described in any one of above <2> to <16>, in which the content of the component (D) is 1% by weight or more, preferably 2% by weight or more, and more preferably 3% by weight or more, and 30% by weight or less, and preferably 15% by weight or less, and more preferably 12% by weight or less in the entire composition.

<18> The cleansing composition described in any one of above <3> to <17>, in which the content of the component (E) is 0.1% by weight or more, and preferably 0.5% by weight or more, and 6% by weight or less, and preferably 3% by weight or less in the total composition.

<19> The cleansing composition described in any one of above <4> to <18>, in which the content of the component (F) is 0.5% by weight or more, and preferably 1% by weight or more, and 3% by weight or less, preferably 2.5% by weight or less, and more preferably 2% by weight or less in the total composition.

<20> The cleansing composition described in any one of above <5> to <19>, in which the content of the component (G) is 0.05% by weight or more, preferably 0.2% by weight or more, and more preferably 0.5% by weight or more, and 10% by weight or less, preferably 6% by weight or less, and more preferably 4% by weight or less in the total composition.

<21> The cleansing composition described in any one of above <1> to <20>, which is a skin cleansing agent.

<22> A method for cleansing skin, comprising applying the cleansing composition described in any one of above <1> to <21> on a body skin part for cleansing followed by rinsing.

<23> Use of the cleansing composition described in any one of above <1> to <20> for production of a skin cleansing agent.

EXAMPLES

In the following examples, methods for measuring various physical properties are as follows.

(1) Measurement of Moisture Content in Pulp and Powder Cellulose:

Moisture content in pulp and powder cellulose was measured by using an infrared moisture tester ("FD-610", manufactured by Kett Electric Laboratory). The point at which the weight change ratio is 0.1% or less for 30 seconds at measurement temperature of 120° C. was taken as the terminal point of measurement.

(2) Calculation of Crystallinity of Pulp and Powder Cellulose

By using "Rigaku RINT 2500VC X-RAY diffractometer" manufactured by Rigaku Corporation, calculation was made based on the following equation (1) from the peak intensity of diffraction spectrum which has been measured according to the following conditions.

X ray source: Cu/Kα-radiation, tube voltage: 40 kV, tube current: 120 mA

Measurement range: 2θ=5 to 45°

Measurement sample: prepared by compressing a pellet with area 320 mm²×thickness 1 mm X ray scan speed: 10°/min If the obtained crystallinity has a negative value, it was all given with crystallinity of 0%.

$$\text{Crystallinity (\%)} = [(I22.6 - I18.5)/I22.6] \times 100 \quad (1)$$

(in the equation, I22.6 indicates diffraction intensity of lattice plane (002 plane) (diffraction angle 2θ=22.6°) and I18.5 indicates diffraction intensity of an amorphous part (diffraction angle 2θ=18.5°) in X ray diffraction).

(3) Calculation of Substitution Degree of Cationized Hydroxypropyl Cellulose (C—HPC):

After purifying C—HPC obtained from Preparation Example by using a dialysis membrane (molecular weight cut of: 1000), the aqueous solution was subjected to freeze-drying to give purified C—HPC. Chlorine content (%) in the obtained purified C—HPC was measured by elemental analysis and, by approximating that the number of cationic groups contained in C—HPC is the same as the number of chloride ions as a counter ion, amount (a (mol/g)) of the cationized ethyleneoxy group (—CH(Y1)-CH(Y2)O—) contained in the unit weight of C—HPC was obtained based on the following equation (2).

$$a(\text{Mol/g}) = \text{Chloride content obtained by elemental analysis }(\%)/(35.5 \times 100) \quad (2)$$

Except that the subject for analysis is purified C—HPC instead of hydroxypropyl cellulose, the content (%) of hydroxypropoxy group was measured according to the "Method for analysis of hydroxypropyl cellulose" described in Japanese Pharmacopoeia. Based on the following equation (3), the content of hydroxypropoxy group (b mol/g) [formula amount (OC$_3$H$_6$OH=75.09] was obtained.

$$b(\text{Mol/g}) = \text{Content of hydroxypropoxy group obtained by gas chromatography analysis }(\%)/(75.09 \times 100) \quad (3)$$

From the obtained values a and b and also the following equations (4) and (5), substitution degree (k) of cationized ethyleneoxy group and substitution degree (m) of propyleneoxy group were calculated.

$$a = k/(162 + k \times K + m \times 58) \quad (4)$$

$$b = m/(162 + k \times K + m \times 58) \quad (5)$$

[in the formula, k and K represent the substitution degree and the formula value, respectively, of a cationized ethyleneoxy group and m represents the substitution degree of a propyleneoxy group].

(4) Calculation of Water Soluble Fractions:

Sample (0.50 g) was weighed in a 50 mL screw tube, and 49.5 g of ion exchange water was added thereto, and dissolved by stirring for 12 hours with a magnetic stirrer. The solution (50 mL) was transferred to a centrifuge tube and centrifuged for 20 minutes at 3000 rpm (2000×g). The supernatant (5 mL) was dried under reduced pressure (105° C., 3 hours) to give a solid matter, and the water soluble fraction was calculated according to the following equation.

Water soluble fraction (%)=(Solid matter weight (g) in 5 mL supernatant×10/Sample weight)×100

(5) Measurement of Average Polymerization Degree (Copper Ammonia Method):

(5-1) Measurement of Viscosity Average Polymerization Degree of Pulp and Powder Cellulose;

(i) Preparation of Solution for Measurement;

To a measuring flask (100 mL), copper (I) chloride (0.5 g) and 25% ammonia water (from 20 to 30 mL) were added. After complete dissolution, copper (II) hydroxide (1.0 g) and 25% ammonia water were added until it is right below the marked line. The resultant was stirred for from 30 to 40 minutes for complete dissolution. After that, precisely weighed cellulose was added and the ammonia water was filled up to the marked line. It was sealed to protect against air and stirred for 12 hours with a magnetic stirrer for dissolution.

As a result, a solution for measurement was prepared. The addition amount of cellulose was changed in the range of from 20 to 500 mg to prepare a solution for measurement with different concentration.

(ii) Measurement of Viscosity Average Polymerization Degree;

The solution for measurement obtained from above (i) (copper ammonia solution) was applied to a Ubbelohde viscometer. After keeping in a thermostat bath (20±0.1° C.) for 1 hour, the liquid flow rate was measured. From the flow time (t (sec)) of copper ammonia solution with various cellulose concentrations (g/dL) and flow time (t0 (sec)) of aqueous copper ammonia solution not including cellulose, the reduced viscosity (ηsp/c) at each concentration was calculated according to the following equation.

$$(\eta sp/c) = \{(t-t0)/t0\}/c$$

(c: cellulose concentration (g/dL))

Further, by extrapolating the reduced viscosity to c=0, intrinsic viscosity [η] (dL/g) was obtained and the viscosity average polymerization degree (DP) was obtained according to the following formula.

$$DP = 2000 \times [\eta]$$

(5-2) Measurement of Viscosity Average Polymerization Degree of C—HPC;

(iii) Preparation of Solution for Measurement;

Except that precisely weighed C—HPC is used instead of precisely weighed cellulose, a solution for measurement was prepared in the same manner as the preparation of a solution for measurement described in the above (i).

(iv) Measurement of Viscosity Average Polymerization Degree;

Except that cellulose equivalent concentration (g/dL) is employed as concentration of a solution for measurement, the measurement was performed in the same manner as the measurement of viscosity average polymerization degree described in above (ii).

As described herein, the concentration (ccell) in terms of cellulose indicates the weight (g) of the cellulose skeleton moiety contained in 1 dL of the solution for measurement, and it is defined by the following equation (6).

$$ccell = u \times 162/(162 + k \times K + m \times 58) \quad (6)$$

[in the equation, u indicates the weight (g) of C—HPC which has been weighed and used for preparation of a solution for measurement, and k, K, and m each are the same as defined in the equation (4) and the equation (5)].

[Substitution Degree of Propyleneoxy Group (—PO—)]

Except that the subject for analysis is C—HPC obtained after purification using a dialysis membrane and freeze-drying instead of hydroxypropyl cellulose, the substitution degree of propyleneoxy group was measured according to the method for analysis of hydroxypropyl cellulose described in Japanese Pharmacopoeia.

Preparation Example 1

Preparation of C—HPC (1)

(1) Chipping Step:

Sheet-shape wood pulp (manufactured by Tembec, average polymerization degree of 1770, crystallinity of 74%, and moisture content of 8.5%) was prepared to be a chip-shape product after treatment using a sheet pelletizer ("SGG-220", manufactured by HORAI Co, Ltd.).

(2) Step of Adding Cationizing Agent and Lowering Crystallinity with an Aid of Mechanical Force:

The obtained chip-shape pulp of 2.1 kg and glycidyl trimethyl ammonium chloride (hereinafter, also referred to as "GMAC", manufactured by Sakamoto Yakuhin Kogyo Co., Ltd., moisture content of 20%, and purity of 90% or higher) of 1.2 kg (0.5 moles per mol of AGU) were mixed with each other in a bag and then supplied to a batch type vibration mill ("FV-20" manufactured by CHUG KAKOHKI Co., Ltd.: total vessel volume of 68.9 L, 114 rods made of SUS304, in which each rod has φ of 30 mm, length of 590 mm, and round cross section, and filling ratio of 70%). By performing a treatment for lowering crystallinity for 12 minutes at frequency number of 20 Hz, total amplitude of 8 mm, and temperature of 30° C. or lower, a powder mixture of cellulose and GMAC (moisture content of 22.3% to cellulose, viscosity average polymerization degree of 1350, and crystallinity of 68%) was obtained.

(3) Step of Adding Base Compound and Lowering Crystallinity with an Aid of Mechanical Force To the powder mixture obtained from the step (2), NaOH powder of 0.284 kg (0.6 moles per mol of AGU) was added and subjected to a treatment for lowering crystallinity for 20 minutes using a batch type vibration mill at frequency number of 20 Hz, total amplitude of 8 mm, and temperature of 50° C. or lower to obtain a powder mixture of cationized cellulose (hereinafter, also referred to as "C-Cell"), GMAC, and NaOH. Further, polypropylene glycol (manufactured by Wako Pure Chemical Industries, Ltd., trade name; "polypropylene glycol diol type average molecular weight of 1000" (PPG1000); weight average molecular weight of 1000) of 0.192 kg (10% by weight per raw cellulose used in the step a) was added to a batch type vibration mill for a treatment of lowering crystallinity for 120 minutes at frequency number of 20 Hz, total amplitude of 8 mm, and temperature of 50° C. or lower to give powder mixture (3.7 kg) of C-Cell, GMAC, NaOH, and PPG1000.

(4) Hydroxypropylation Step and Neutralization Step:

Powder mixture (10.0 kg) prepared by repeating several times the process (2) and the process (3) was added to a Pro Share mixer (75 L). After increasing the internal temperature to 56° C., 2.8 kg of propylene oxide (1.5 moles per mol of AGU) was sequentially added dropwise so that the reaction was performed until the internal pressure decreases according to consumption of propylene oxide. To 12.6 kg of the reaction product, 8.0 kg of 24% aqueous solution of lactic acid was added by spraying to give 20.6 kg of neutralization product.

The obtained neutralization product (15.2 kg) was added to a 65 L high speed mixer and dried under reduced pressure at internal temperature of from 70 to 80° C. to obtain the dry product (10.0 kg). The resulting dry product was pulverized by a pin mill and used as a powder.

The product was purified using a dialysis membrane (molecular weight cut off: 1000), and the aqueous solution was subjected to freeze-drying to give purified C—HPC (1). As a result of the analysis of the purified product, the substitution degree of the cationic group and propyleneoxy group was found to be 0.22 and 1.13, respectively. Further, the viscosity average polymerization degree of the obtained C—HPC (1) was found to be 693.

Preparation Example 2

Preparation of C—HPC (2)

(1) Chipping Step:

Sheet-shape wood pulp (Biofloc HV+ manufactured by Tembec, average polymerization degree of 1481, crystallinity of 74%, and moisture content of 4.6%) was prepared to be a chip-shape product (width and length; 3 to 5 mm) after treatment using a sheet pelletizer ("SGG-220", manufactured by HORAI Co, Ltd.).

(2) Step of Obtaining Alkali Cellulose

The chip-shape pulp (100 g) obtained from the above step (1) and 23.6 g of 0.7 mm particulate NaOH (equivalent to 1.0 moles per mol of AGU) were supplied to a batch type vibration mill ("MB-1" manufactured by CHUO KAKOHKI Co., Ltd.: total vessel volume of 3.5 L, 13 rods made of SUS304, in which each rod has φ of 30 mm, length of 218 mm, and round cross section, and filling ratio of 57%). After performing pulverizing treatment for 15 minutes (frequency number of 20 Hz, amplitude of 8 mm, and temperature of from 30 to 70° C.), the resulting mixture product of cellulose and NaOH was transferred to a mortar and 50 g of water was added thereto by spraying. It was then mixed for 5 minutes at 20° C. using a pestle and mortar to give alkali cellulose (average polymerization degree: 1175, crystallinity: 28%).

(3) Hydroxypropylation Step

The alkali cellulose obtained from the step (2) was added to a sealed reactor (manufactured by Nitto Koatsu, 1.5 L autoclave) and the inside of the reaction vessel was replaced with nitrogen. Subsequently, propylene oxide was sequentially added while stirring at constant inside vessel pressure of 0.05 MPa after increasing temperature to 50° C. followed by the reaction for 7 hours. The total addition amount of propylene oxide was 102 g (equivalent to 3.0 moles per mol of AGU).

(4) Cationizing Step:

The reaction mixture (30.0 g) obtained from the above step (3) was transferred to a mortar and 9.30 g (equivalent to 0.50 moles per mol of AGU) of 65% aqueous solution of 3-chloro-2-hydroxypropyltrimethyl ammonium chloride (manufactured by Yokkaichi Chemical Co., Ltd.) was added, followed by stirring for 5 min. After transfer to a 150 mL glass bottle, the reaction was allowed to occur for 7 hours at 50° C. to give crude C—HPC.

The crude C—HPC powder (5.0 g) was collected and neutralized with lactic acid. For the purpose of obtaining substitution degrees of the propyleneoxy group and cationized ethyleneoxy group, the neutralization product was purified by using a dialysis membrane (molecular weight cut off: 1000) and the aqueous solution was subjected to freeze-drying to give purified C—HPC (2).

As a result of the analysis of the purified product, the substitution degree of the cationic group and propyleneoxy group were found to be 0.18 and 2.0, respectively. Further, the viscosity average polymerization degree of the obtained C—HPC (2) was found to be 693.

Preparation Example 3

Preparation of C—HPC (3)

(1) Chipping Step:

Sheet-shape wood pulp (Biofloc HV+ manufactured by Tembec, average polymerization degree of 1604, α-cellulose content of 93.0%, crystallinity of 74%, and moisture content of 7.0%) was prepared to be a chip-shape product (width and length; from 3 to 5 mm) after treatment using a sheet pelletizer ("SGG-220", manufactured by HORAI Co, Ltd.).

The obtained chip-shape pulp was added to a vacuum dryer (product name: VO-402, manufactured by Advantec Toyo Kaisha, Ltd.) and dried for 2 hours at 105° C., 20 kPa under nitrogen stream to give dry chip-shape pulp (average polymerization degree: 1604, α-cellulose content: 99.2%, crystallinity: 74%, and moisture content: 0.8%).

(2) Step of Obtaining Alkali Cellulose (Step 1)

The obtained dry chip-shape pulp (920 g) was supplied to a vibration rod mill ("FV-10" manufactured by CHUO KAKOHKI Co., Ltd.: total vessel volume of 35 L, 63 rods are used in which each rod has diameter of 30 mm). After performing pulverizing treatment for 10 minutes (20 Hz, amplitude of 8 mm, and temperature of from 10 to 40° C.), powdery pulp with lowered crystallinity (920 g, average polymerization degree: 1198, crystallinity: 14%, moisture content: 1.0%) was obtained as cellulose-containing raw material (II).

(Step 2)

Powdery pulp (460 g) obtained from above (Step 1) as cellulose-containing raw material (II) was supplied to a mixer ("Redige mixer" with volume of 5 L, manufactured by MATSUBO Corporation), and while being stirred with main wing at 250 rpm and chopper wing at 2500 rpm, 42.5% aqueous solution of sodium hydroxide (266.8 g (equivalent to 1.0 mole per mol of AGU of raw material (II) cellulose, and 33% of water per raw material (II) cellulose)) was added for 1.5 minutes by spraying. After the spraying, the internal temperature was increased to 50° C. and aged while stirring for 3 hours to obtain an alkali cellulose mixture.

(3) Hydroxypropylation Step:

The alkali cellulose mixture (720.5 g) obtained from above (2) was added to the above-mentioned Redige mixer and the temperature was increased to 50° C. while being stirred with main wing at 50 rpm and chopper wing at 400 rpm. After that, propylene oxide (571.4 g, equivalent to 3.5 moles per mol of AGU of the alkali cellulose) was added dropwise thereto for 3.5 hours. Once the dropwise addition was completed, it was aged for 2 hours at 50° C.

(4) Cationizing Step and Neutralization Step:

The reaction mixture (272.0 g) obtained from the hydroxypropylation was added to a mixer ("High Speed Mixer" with 2 L volume, manufactured by Fukae Pautec, Co., Ltd.). After increasing the internal temperature to 50° C., 65% aqueous solution of 3-chloro-2-hydroxypropyltrimethyl ammonium chloride (manufactured by Yokkaichi Chemical Co., Ltd.) (82.8 g, equivalent to 0.5 moles per mol of AGU which constitutes the cellulose skeleton of the compound containing cellulose skeleton in the reaction mixture that has been obtained by hydroxypropylation) was added for 1.5 minutes by spraying while being stirred with main wing at 337 rpm and chopper wing at 1800 rpm. After spraying, aging while stirring was performed for 2 hours to give crude C—HPC. Subsequently, 29% aqueous solution of lactic acid was sprayed for 1.5 minutes for neutralization of the crude C—HPC.

The crude C—HPC powder (5.0 g) was collected. For the purpose of obtaining substitution degrees of the propyleneoxy group and cationized ethyleneoxy group, the neutralization product was purified by using a dialysis membrane (molecular weight cut off: 1000) and the aqueous solution was subjected to freeze-drying to give purified C—HPC (3).

As a result of the analysis of the purified product, the substitution degrees of the cationic group and the propyleneoxy group were found to be 0.11 and 2.0, respectively. Further, the viscosity average polymerization degree of the obtained C—HPC (3) was found to be 743.

Preparation Example 4

Preparation of C—HPC (4)

(1) Chipping Step:

As cellulose, sheet-shape wood pulp (manufactured by Tembec, viscosity average polymerization degree of 1770, crystallinity of 74%, and moisture content of 7.6%) was prepared to be a chip-shape product after treatment using a sheet pelletizer ("SGG-220", manufactured by HORAI Co, Ltd.).

(2) Step of Adding Cationizing Agent and Lowering Crystallinity with an Aid of Mechanical Force:

The obtained chip-shape pulp (108 g) and glycidyl trimethyl ammonium chloride (hereinafter, also referred to as "GMAC", manufactured by Sakamoto Yakuhin Kogyo Co., Ltd., moisture content of 20%, and purity of 90% or higher) (23.4 g) (0.2 moles per unit mol of the anhydroglucose in cellulose (hereinafter, also referred to as "AGU")) were mixed with each other using a pestle and mortar and then supplied to a batch type vibration mill ("MB-1" manufactured by CHUO KAKOHKI Co., Ltd.: total vessel volume of 3.5 L, 13 rods made of SUS304, in which each rod has $\phi$ of 30 mm, length of 218 mm, and round cross section, and filling ratio of 57%). By performing a treatment for lowering crystallinity for 12 minutes at frequency number of 20 Hz, total amplitude of 8 mm, and temperature of 30° C. or lower, a powder mixture (131 g) of cellulose and GMAC (moisture content of 12.3% to cellulose, viscosity average polymerization degree of 1350, and crystallinity of 68%) was obtained.

(3) Step of Adding Base Compound and Lowering Crystallinity with an Aid of Mechanical Force:

The powdery pulp (131 g) obtained from above (2) was mixed with 24.7% aqueous sodium hydroxide solution (20 g, 0.2 moles per mol of AGU) using a pestle and mortar, and then supplied to a batch type vibration mill ("MB-1" manufactured by CHUO KAKOHKI Co., Ltd.: total vessel volume of 3.5 L, 117 rods made of SUS304, in which each rod has $\phi$ of 10 mm, length of 218 mm, and round cross section, and filling ratio of 57%). By performing a treatment for lowering crystallinity for 60 minutes at frequency number of 20 Hz, total amplitude of 8 mm, and temperature of 30° C. or lower, a powder mixture (151 g) of C-Cell, GMAC, and sodium hydroxide (moisture content of 27.4% to cellulose, viscosity average polymerization degree of 1330, and crystallinity of 45%) was obtained. The powdery mixture (5 g) was collected, neutralized with acetic acid, and washed three times with 85% aqueous solution of isopropyl alcohol (100 mL) for desalting and purification. Subsequently, according to drying under reduced pressure, purified cationized cellulose (4 g, viscosity average polymerization degree: 1330, crystallinity: 45%) was obtained.

As a result of the elemental analysis, the substitution degree of cationic group was calculated to be 0.1. Further, the water soluble fraction was 31%.

(4) Hydroxypropylation Step and Neutralization Step:

The obtained cationized cellulose (100 g, non-neutralized and non-purified product) was injected to a 1 L kneader equipped with a reflux condenser (PNV-1 type, manufactured by IRIE SHOKAI Co., Ltd.). The jacket part of the kneader was heated to 70° C. by hot water and propylene oxide (141.9 g, 6 moles per mol of AGU, manufactured by Kanto Chemical Co., Inc., special grade reagent) was added dropwise thereto under nitrogen atmosphere and the reaction was performed for 40 hours until the reflux stops according to consumption of propylene oxide.

The product was collected from the kneader to give crude C—HPC powder with pale brown color (240 g). 10.0 g of the reaction product was collected and neutralized with acetic acid to give a pale brown solid. The product was purified by using a dialysis membrane (molecular weight cut off: 1000) and the aqueous solution was subjected to freeze-drying to give purified C—HPC (4).

From the content of the propyleneoxy group [molecular weight ($C_3H_6O$)=58.08] obtained by the hydroxypropyl cellulose analysis, the substitution degree of the propyleneoxy group was found to be 2.9. Further, the water soluble fraction of the obtained C—HPC (4) was found to be 71% and the viscosity average polymerization degree was found to be 1,300.

Preparation Example 5

Preparation of C—HPC (5)

(1) Preparation of Dry Powder Cellulose:

Powder cellulose (manufactured by NIPPON PAPER Chemicals Co., Ltd., cellulose powder KC FLOCK W-400G, average polymerization degree: 191, crystallinity: 77%, and moisture content: 7.0%) was dried for 12 hours at 50° C. under reduced pressure to obtain dry powder cellulose (moisture content: 1.0%).

(2) Cationizing Step (1):

The obtained powder cellulose (100.0 g) was mixed with GMAC (60.8 g) using a pestle and mortar and added to the vibration mill described in Preparation Example 1. After pulverization treatment for 12 minutes (frequency number of 20 Hz, total amplitude of 8 mm, and temperature of from 10 to 40° C.), powdery mixture of cellulose and GMAC was obtained.

Further, 48% aqueous solution of sodium hydroxide (29.8 g) was added to the vibration mill, and a pulverization treatment under the same pulverization condition using the vibration mill was performed for 60 minutes to give cationized cellulose.

(3) Hydroxypropylation Step:

A kneader to which the cationized cellulose (190 g) obtained from the above step was added was heated to 70° C., and then propylene oxide (18.0 g) was added dropwise while stirring, and the reaction was allowed to occur for 6 hours until the reflux stops according to consumption of propylene oxide.

(4) Cationizing Step (2):

The mixture after the reaction was transferred from the kneader to a pestle and mortar, added with GMAC (87.5 g, equivalent to 0.8 moles per mol of AGU), and stirred for 10 minutes at room temperature. After that, it was brought back to the kneader, and the reaction was performed while stirring for 5 hours at 50° C. to give crude C—HPC powder with pale brown color (295 g).

To the obtained crude C—HPC powder, GMAC (87.5 g) was added again, and the procedure up to the reaction at 50° C. was similarly carried out. The above procedures were repeated seven times in total (total amount of the added propylene oxide was 612.5 g; equivalent to 5.3 moles per mol of AGU). The reaction product (10.0 g) was collected and neutralized with lactic acid to obtain pale brown solid. For the purpose of obtaining substitution degrees of the propyleneoxy group and cationized ethyleneoxy group, the product was purified by using a dialysis membrane (cut off molecular weight: 1000) and the aqueous solution was subjected to freeze-drying to give purified C—HPC (5).

As a result of the analysis of the purified product, the substitution degrees of the cationized ethyleneoxy group and propyleneoxy group in the obtained purified C—HPC (5) were found to be 2.36 and 0.2, respectively. Further, the average polymerization degree was found to be 432.

Preparation Example 6

Preparation of C—HPC (6)

(1) Chipping Step:

Sheet-shape wood pulp (Biofloc HV+ manufactured by Tembec, average polymerization degree of 1604, α-cellulose content of 93.0%, crystallinity of 74%, and moisture content of 7.0%) was prepared to be a chip-shape product (width and length; from 3 to 5 mm) after treatment using a sheet pelletizer ("SGG-220", manufactured by HORAI Co, Ltd.).

The obtained chip-shape pulp was added to a vacuum dryer (product name: VO-402, manufactured by Advantec Toyo Kaisha, Ltd.) and dried for 2 hours at 105° C., 20 kPa under nitrogen stream to give dry chip-shape pulp (average polymerization degree: 1604, α-cellulose content: 99.2%, crystallinity: 74%, and moisture content: 0.8%).

(2) Step of Obtaining Alkali Cellulose (Step 1)

The obtained dry chip-shape pulp (920 g) was supplied to a vibration rod mill ("FV-10" manufactured by CHUO KAKOHKI Co., Ltd.: total vessel volume of 35 L, 63 rods are used in which each rod has diameter of 30 mm). After performing pulverizing treatment for 10 minutes (frequency number of 20 Hz, amplitude of 8 mm, and temperature of from 10 to 40° C.), powdery pulp with lowered crystallinity (920 g, average polymerization degree: 1198, crystallinity: 14%, moisture content: 1.0%) was obtained as cellulose-containing raw material (II).

(Step 2)

Powdery pulp (460 g) obtained from above (Step 1) as cellulose-containing raw material (II) was supplied to a mixer ("Redige mixer" with volume of 5 L, manufactured by MATSUBO Corporation), and while being stirred with main wing at 250 rpm and chopper wing at 2500 rpm, 42.5% aqueous solution of sodium hydroxide (266.8 g (equivalent to 1.0 mole per mol of AGU of raw material (II) cellulose, and 33% of water per raw material (II) cellulose)) was added for 1.5 minutes by spraying. After the spraying, the internal temperature was increased to 50° C. and aged while stirring for 3 hours to obtain an alkali cellulose mixture.

(3) Hydroxypropylation Step:

The alkali cellulose mixture (720.5 g) obtained from above (2) was added to a Redige mixer and the temperature was increased to 50° C. while being stirred with main wing at 50 rpm and chopper wing at 400 rpm. After that, propylene oxide (571.4 g, equivalent to 3.5 moles per mol of AGU of the alkali cellulose) was added dropwise thereto for 3.5 hours. Once the dropwise addition is completed, it was aged for 2 hours at 50° C.

(4) Cationizing Step and Neutralization Step:

The reaction mixture obtained from the hydroxypropylation step was aged by keeping it for 6 months in a refrigerator (5° C.) to have slow degradation of sugar chain. The reaction mixture after low temperature aging (5.0 g) and 65% aqueous solution of 3-chloro-2-hydroxypropyltrimethyl ammonium chloride (manufactured by Yokkaichi Chemical Co., Ltd.) (1.38 g, equivalent to 0.45 moles per mol of AGU which constitutes the cellulose skeleton of the compound containing cellulose skeleton in the reaction mixture that has been obtained by hydroxypropylation) were mixed with each other using a pestle and mortar, and aged by keeping it for 5 hours in a sealed reactor (50° C.) to prepare crude C—HPC. Subsequently, 29% aqueous solution of lactic acid was used for neutralization of the crude C—HPC.

The crude C—HPC powder (2.0 g) was collected. For the purpose of obtaining substitution degrees of the propyleneoxy group and cationized ethyleneoxy group, the neutralization product was purified by using a dialysis membrane (cut off molecular weight: 1000) and the aqueous solution was subjected to freeze-drying to give purified C—HPC (6).

As a result of the analysis of the purified product, the substitution degrees of the cationic group and the propyleneoxy group were found to be 0.20 and 2.1, respectively. Further, the viscosity average polymerization degree of the obtained C—HPC (6) was found to be 100.

TABLE 1

|  |  | Average polymerization degree | Substitution degree of cationized EO *1 | Substitution degree of PO *2 |
|---|---|---|---|---|
| Preparation Example 1 | C-HPC(1) | 693 | 0.22 | 1.13 |
| Preparation Example 2 | C-HPC(2) | 693 | 0.18 | 2.0 |
| Preparation Example 3 | C-HPC(3) | 743 | 0.11 | 2.0 |
| Preparation Example 4 | C-HPC(4) | 1300 | 0.10 | 2.9 |
| Preparation Example 5 | C-HPC(5) | 432 | 2.36 | 0.2 |
| Preparation Example 6 | C-HPC(6) | 100 | 0.20 | 2.1 |

*1: Substitution degree of cationized ethyleneoxy group (p)
*2: Substitution degree of propyleneoxy group (q)

Preparation Example 7

Preparation of Sodium Polyoxyethylene (2) Lauryl Ether Carboxylate

According to EO reaction of lauryl alcohol with a raw material, alkyl ethoxylate with EO addition mole number of 3.05 moles was obtained.

To a glass reaction vessel having stirring and temperature control function and equipped with an oxygen inlet tube, the above product (90 g, 0.2 moles) and 48% aqueous solution of sodium hydroxide (16.7 g, 0.2 moles as sodium hydroxide), a palladium-platinum-bismuth catalyst (0.9 g, palladium (4%), platinum (1%), and bismuth (5%) are supported on active carbon, moisture content: 50%), and water (494.4 g) were introduced, respectively. While stirring condition, the liquid temperature was increased to 70° C., and while purging oxygen (at ratio of 27% by mol (relative to produced AE/time), the catalytic oxidation was performed for 3.5 hours at 70° C.

Once the reaction is completed, the catalyst was removed from the reaction liquid by filtration, and thus an aqueous solution of sodium alkyl ether carboxylate was obtained. Subsequently, it was dried to powder, which was then used as EC(A).

Preparation Example 8

Preparation of Sodium Polyoxyethylene (3) Lauryl Ether Carboxylate

According to EO reaction between lauryl alcohol and a raw material as described in Preparation Example 7, alkyl ethoxylate with EO addition mole number of 4.05 moles was obtained. It was then subjected to an oxidation in the same manner as Preparation Example 7. The obtained sodium alkyl ether carboxylate was dried to powder, which was then used as EC(B).

Examples 1 to 13 and Comparative Examples 1 to 3

The skin cleansing composition having the composition shown in Table 2 was produced according to the following method. Quickness of lathering, foam quality, foam volume during cleansing, low slimy feel during rinsing, easy disappearance of slimy feel during rinsing, strength of a stop feeling property after rinsing, and skin feel immediately after towel blotting and skin feel after drying were evaluated for the obtained skin cleansing composition. The results are also shown in Table 2.

(Preparation Method)

After dispersing powdery C—HPC in water at 20° C., each component was mixed in order, fully stirred, and dissolved to give a skin cleansing composition.

(Evaluation Method)

(1) Quickness of Lathering:

Each cleansing composition (1 g) was collected by hands, diluted by five times approximately with tap water at 30° C. After briefly generating foams for 5 seconds with both hands, quickness of lathering was evaluated. The evaluation was made based on the following criteria, and expressed as an average value given by five professional panelists.

5; It was felt that the lathering (ability) was very fast.
4; It was felt that the lathering (ability) was fast.
3; It was felt that the lathering (ability) was moderate.
2; It was felt that the lathering (ability) was slightly slow.
1; It was felt that the lathering (ability) was slow.

(2) Foam Quality (Creaminess):

Each cleansing composition (1 g) was collected by hands, diluted by five times approximately with tap water at 30° C. After briefly generating foams for 20 seconds with both hands, foam quality (creaminess) was evaluated. The evaluation was made based on the following criteria, and expressed as an average value given by five professional panelists.

5; It was felt that foam quality was fine, very creamy, and thus the foam quality was found to be good.
4; It was felt that foam quality was creamy, and thus the foam quality was found to be good.
3; It was felt that foam quality was slightly creamy.
2; It was felt that foam quality was slightly light and rough.
1; It was felt that foam quality was light and rough.

(3) Foam Volume During Cleansing:

Each cleansing composition was diluted with tap water at high ratio (that is, 20-fold dilution, presumably equivalent to the condition upon having foam dissipation after rinsing) to provide a sample aqueous solution. The sample aqueous solution (7.5 mL) was placed in a graduated 50 mL glass cylinder (35 mm×78 mm) equipped with a cock, and the cock was put thereon. Using a shaker (manufactured by Iwaki Sangyo K.K.; Model No.: "UNIVERSAL SHAKER V-SX"), the cylinder was shaken for 30 seconds at a rate of 300 strokes/min, and immediately after the completion of the shaking, the volume of foam was read (cm).

(4) Low Slimy Feel During Rinsing:

Each cleansing composition (1 g) was collected by one hand, and diluted by five times approximately with tap water at 30° C. After briefly generating foams for 20 seconds with both hands, the foams were collected in palm of one hand and used for cleansing the other arm (that is, from elbow to wrist). After cleansing, foams on the cleansed arm were washed off twice with tap water (12 mL) in the hand used for cleansing. At that time, strength of slimy feel was evaluated by five professional panelists. The evaluation was made based on the following criteria, and expressed as an average value given by five professional panelists.

5; there was almost no slimy feel.
4; there was weak slimy feel.
3; there was slimy feel.
2; there was somewhat strong slimy feel.
1; there was strong slimy feel.

(5) Easy Disappearance of Slimy Feel During Rinsing:

Each cleansing composition (1 g) was collected by one hand, and diluted by five times approximately with tap water at 30° C. After briefly generating foams for 20 seconds with both hands, the foams were collected in palm of one hand and used for cleansing the other arm (that is, from elbow to wrist). After cleansing, foams on the cleansed arm were washed off twice by spraying tap water (12 mL) in the hand used for cleansing. Again, tap water was sprayed at flow rate of 100 mL/min onto the arm, and at the same time both forearms were rubbed once per sec for rinsing, and the number of the rubbing until stop feeling was sensed was counted. The measurement results were ranked according to the following evaluation criteria and expressed as an average value given by five professional panelists.

5; number of rubbing was less than 3
4; number of rubbing was 3 or more but less than 6
3; number of rubbing was 6 or more but less than 9
2; number of rubbing was 9 or more but less than 12
1; number of rubbing was more than 12

(6) Strength of a Stop Feeling Upon Completion of Rinsing (Evaluation Based on Whole Body Washing)

Ten professional panelists washed their body using each cleansing composition. The number of the people who replied that the stop feeling is strong upon the completion of rinsing was counted.

(7) Skin Feel Right Immediately after Towel Blotting:

Ten professional panelists washed their body using each cleansing composition. Right after towel blotting, the inside of one arm was examined using palm of the other hand in terms of moist feeling like the hands adsorbing onto the skin. The number of the people who replied that the there is strong moistness like the hands adsorbing onto the skin was counted.

(8) Skin Feel after Drying (Flexible Elasticity):

Ten professional panelists washed their body using each cleansing composition. Ten minutes after towel blotting of skin, the number of the people who replied that the there is strong flexible elasticity was counted.

(9) Skin Feel after Drying (Natural Moistness):

Ten professional panelists washed their body using each cleansing composition. Ten minutes after towel blotting of skin, the number of the people who replied that the there is strong natural moistness without sticky feeling was counted.

TABLE 2

| | Component (% by weight) | Example 1 | 2 | 3 | 4 | 5 | 6 | 7 | 8 | 9 |
|---|---|---|---|---|---|---|---|---|---|---|
| (A) | sodium polyoxyethylene (2.6) lauryl ether carboxylate *1 | 5.00 | 5.00 | 5.00 | 5.00 | 5.00 | 5.00 | 5.00 | 1.80 | 2.00 |
| (B) | C-HPC (1) (cationizing degree: 0.22, PO substitution degree: 1.13) | 0.60 | 0.60 | 0.60 | 0.60 | 0.60 | 0.60 | 0.60 | 1.80 | 1.00 |
| | C-HPC (2) (cationizing degree: 0.18, PO substitution degree: 2.0) | | | | | | | | | |
| | C-HPC (4) (cationizing degree: 0.1, PO substitution degree: 2.9) | | | | | | | | | |
| (C) | water | balance | balance | balance | balance | balance | balance | balance | balance | balance |
| (D) | sodium polyoxyethylene (1) lauryl ether sulfate *2 | | 3.00 | 3.00 | 3.00 | 3.00 | 3.00 | 3.00 | | |
| (E) | sodium chloride | | | 1.00 | | 1.00 | 1.00 | 1.00 | | |
| | sodium malate | | | | 1.00 | | | | | |
| (F) | distearic acid ethylene glycol (pearlescent agent) *3 | | | | | 1.60 | 1.60 | 1.60 | | |
| (G) | lauryl glucoside *4 | | | | | | | 3.20 | 3.20 | |
| (H) | lauric acid amide propylbetaine *5 | | | | | | | | 2.90 | |
| | sodium polyoxyethylene (10) lauryl ether carboxylate *6 | | | | | | | | | |
| | hydroxyethyl cellulose hydroxypropyl trimethyl ammonium chloride ether *7 | | | | | | | | | |
| | pH adjuster | q.s. | q.s. | q.s. | q.s. | q.s. | q.s. | q.s. | q.s. | q.s. |
| | Total | 100 | 100 | 100 | 100 | 100 | 100 | 100 | 100 | 100 |
| | (B)/(A) weight ratio | 0.12 | 0.12 | 0.12 | 0.12 | 0.12 | 0.12 | 0.12 | 1.00 | 0.50 |
| | (E)/((A) + (B) + (D)) | — | — | 0.12 | 0.12 | 0.10 | 0.10 | 0.10 | — | — |
| | pH(20 times dilution) | 5.9 | 5.8 | 5.8 | 5.8 | 5.7 | 5.8 | 5.8 | 5.9 | 5.9 |
| | quickness of lathering | 3.4 | 4.4 | 4.4 | 4.4 | 4.4 | 4.4 | 4.6 | 3 | 3.4 |
| | foam quality (creaminess) | 4 | 4.2 | 4.2 | 4.2 | 4.2 | 4.4 | 4.6 | 3.4 | 4 |
| | foam volume during cleansing (cm) | 3.3 | 4.4 | 4.2 | 4.3 | 4.4 | 4.8 | 5 | 2.4 | 2.6 |
| | low slimy feel during rinsing | 4.8 | 4.4 | 4.4 | 4.4 | 4.4 | 4.4 | 4.4 | 4.4 | 4.6 |
| | easy disappearance of slimy feel during rinsing | 4.2 | 4.6 | 4.6 | 4.6 | 4.6 | 4.6 | 4.6 | 4 | 4.2 |
| | strength of stop feeling property after finishing rinsing (number of people) | 7 | 9 | 10 | 9 | 10 | 9 | 9 | 6 | 7 |
| | skin feel right after towel blotting; moist feeling like the hands adsorbing onto the skin (number of people) | 8 | 8 | 8 | 8 | 8 | 9 | 9 | 7 | 8 |
| | skin feel after drying; flexible elasticity (number of people) | 6 | 6 | 7 | 7 | 7 | 7 | 7 | 6 | 6 |
| | skin feel after drying; natural moistness (number of people) | 7 | 8 | 8 | 8 | 9 | 9 | 9 | 7 | 7 |

| | Component (% by weight) | Example 10 | 11 | 12 | 13 | Comparative Example 1 | 2 | 3 |
|---|---|---|---|---|---|---|---|---|
| (A) | sodium polyoxyethylene (2.6) lauryl ether carboxylate *1 | 6.00 | 10.00 | 5.00 | 5.00 | | 5.00 | 5.00 |
| (B) | C-HPC (1) (cationizing degree: 0.22, PO substitution degree: 1.13) | 0.40 | 0.30 | | | 0.60 | | |
| | C-HPC (2) (cationizing degree: 0.18, PO substitution degree: 2.0) | | | 0.60 | | | | |
| | C-HPC (4) (cationizing degree: 0.1, PO substitution degree: 2.9) | | | | 0.60 | | | |
| (C) | water | balance | balance | balance | balance | balance | balance | balance |
| (D) | sodium polyoxyethylene (1) lauryl ether sulfate *2 | | | | | | | 3.00 |
| (E) | sodium chloride | | | | | | | |
| | sodium malate | | | | | | | |
| (F) | distearic acid ethylene glycol (pearlescent agent) *3 | | | | | | | |
| (G) | lauryl glucoside *4 | | | 3.20 | 3.20 | | | |

TABLE 2-continued

|  |  |  |  |  |  |  |  |  |
|---|---|---|---|---|---|---|---|---|
| (H) | lauric acid amide propylbetaine *5 |  |  |  | 2.90 | 2.90 |  |  |
|  | sodium polyoxyethylene (10) lauryl ether carboxylate *6 |  |  |  |  |  | 5.00 |  |
|  | hydroxyethyl cellulose hydroxypropyl trimethyl ammonium chloride ether *7 |  |  |  |  |  |  | 0.60 |
|  | pH adjuster | q.s. | q.s. | q.s. | q.s. | q.s. | q.s. | q.s. |
|  | Total | 100 | 100 | 100 | 100 | 100 | 100 | 100 |
|  | (B)/(A) weight ratio | 0.07 | 0.03 | 0.12 | 0.12 | — | — | — |
|  | (E)/((A) + (B) + (D)) | — | — | — | — | — | — | — |
|  | pH(20 times dilution) | 5.9 | 5.9 | 5.8 | 5.8 | 5.8 | 5.7 | 5.7 |
|  | quickness of lathering | 3.4 | 3.6 | 3.6 | 3.6 | 2.4 | 4.2 | 3.8 |
|  | foam quality (creaminess) | 4 | 3.8 | 4.2 | 4.2 | 2.8 | 3.6 | 3.2 |
|  | foam volume during cleansing (cm) | 3.5 | 4 | 3.4 | 3.5 | 2.4 | 4.5 | 5.2 |
|  | low slimy feel during rinsing | 4.8 | 4.4 | 4.8 | 4.8 | 2.4 | 1.8 | 2.6 |
|  | easy disappearance of slimy feel during rinsing | 4.2 | 4 | 4.8 | 5 | 2.2 | 1.4 | 3.8 |
|  | strength of stop feeling property after finishing rinsing (number of people) | 7 | 6 | 9 | 9 | 2 | 2 | 6 |
|  | skin feel right after towel blotting; moist feeling like the hands adsorbing onto the skin (number of people) | 8 | 7 | 8 | 8 | 2 | 5 | 1 |
|  | skin feel after drying; flexible elasticity (number of people) | 6 | 6 | 6 | 6 | 6 | 5 | 3 |
|  | skin feel after drying; natural moistness (number of people) | 7 | 7 | 8 | 8 | 3 | 5 | 1 |

*1: manufactured by Kao Corporation, effective component of AKYPO 26 (mixture of sodium polyoxyethylene (2.6) lauryl ether carboxylate and sodium polyoxyethylene (2.6) myristyl ether carboxylate)
*2: manufactured by Kao Corporation, effective component of EMAL 170J
*3: manufactured by Kao Corporation, effective component of EMANON 3201MH-V
*4: manufactured by Kao Corporation, effective component of AG-124
*5: manufactured by Kao Corporation, effective component of AMPHITOL 20AB
*6: manufactured by Kao Corporation, effective component of KAOAKYPO RLM-100NV
*7: manufactured by Dow Company, effective component of UCARE POLYMER LR400 (cation charge density 1 meq/g)

Examples 14 to 23

The cleansing composition having the composition shown in Table 3 was produced in the same manner as Examples 1 to 13.

All the obtained cleansing compositions were found to have a fast lathering ability, foam quality with fine texture, high creaminess, high foam increasing property during cleansing, excellent use feel during cleansing, strong stop feeling due to no slimy feel during rinsing and quick disappearance of slimy feel, and after drying, flexible elasticity and natural moist feeling.

TABLE 3

|  |  | Example |  |  |  |  |  |  |  |  |  |
|---|---|---|---|---|---|---|---|---|---|---|---|
|  | component (% by weight) | 14 | 15 | 16 | 17 | 18 | 19 | 20 | 21 | 22 | 23 |
| (A) | Sodium polyoxyethylene (2.6) lauryl ether carboxylate *1 | 1.00 |  | 2.00 | 2.00 | 2.00 |  | 10.00 | 4.00 | 6.00 | 2.00 |
|  | EC (A) (EO addition mole number: 2.0) |  |  |  | 2.00 | 3.00 | 2.00 | 5.00 | 1.00 | 5.00 |  |
|  | EC (B) (EO addition mole number: 3.0) |  | 1.50 | 2.00 | 2.00 |  | 2.00 | 5.00 |  |  |  |
| (B) | C-HPC (1) cationizing degree: 0.22, PO substitution degree: 1.13) | 1.00 | 0.02 |  |  | 1.00 |  | 2.00 | 0.20 |  | 0.30 |
|  | C-HPC (2) cationizing degree: 0.18, PO substitution degree: 2.0) |  |  | 1.00 | 1.00 | 1.00 | 0.20 | 2.00 | 0.30 |  |  |
|  | C-HPC (3) cationizing degree: 0.11, PO substitution degree: 2.0) |  |  |  | 0.50 |  |  | 2.00 |  | 0.50 |  |
|  | C-HPC (4) cationizing degree: 0.1, PO substitution degree: 2.9) | 0.50 |  |  | 0.50 |  |  | 2.00 | 0.50 | 0.30 |  |
|  | C-HPC (5) cationizing degree: 2.36, PO substitution degree: 0.2) | 0.50 |  |  |  |  |  | 2.00 |  | 0.20 |  |
|  | C-HPC (6) cationizing degree: 0.2, PO substitution degree: 2.1) |  |  |  |  |  |  |  |  |  | 0.20 |
| (C) | water | balance | balance | balance | balance | balance | balance | balance | balance | balance | balance |
| (D) | sodium polyoxyethylene (1) lauryl ether sulfate *2 |  | 2.00 | 10.00 | 1.00 | 0.50 |  | 0.50 | 4.00 |  | 100 |
|  | sodium polyoxyethylene (2) lauryl ether sulfate *3 |  | 1.00 |  | 1.00 | 0.50 |  |  | 1.00 |  |  |
|  | Sodium polyoxyethylene (4.5) lauryl ether carboxylate *4 |  |  |  |  |  |  |  |  |  |  |
|  | potassium laurate | 3.00 |  |  |  | 3.00 |  | 0.50 |  | 1.00 |  |
|  | potassium myristate | 9.00 |  |  |  | 5.00 |  |  |  | 4.00 |  |
|  | potassium palmitate | 12.00 |  |  |  | 3.00 |  |  |  | 2.00 |  |
|  | potassium stearate | 6.00 |  |  |  |  |  |  |  |  |  |
|  | sodium cocoyl glutamate *5 |  | 12.00 |  |  |  | 7.00 |  |  |  |  |
| (E) | sodium chloride | 0.10 | 0.30 | 3.00 | 3.00 | 0.20 | 0.10 | 3.00 |  | 0.50 |  |
|  | sodium malate | 0.40 | 0.20 | 3.00 |  |  |  |  | 0.10 |  | 0.50 |
| (F) | distearic acid ethylene glycol (pearlescent agent) *6 | 0.50 | 1.00 | 2.00 | 2.50 | 1.00 | 2.00 | 3.00 | 1.50 | 1.00 | 1.00 |

TABLE 3-continued

| component (% by weight) | | 14 | 15 | 16 | 17 | 18 | 19 | 20 | 21 | 22 | 23 |
|---|---|---|---|---|---|---|---|---|---|---|---|
| (G) | alkyl (C10-16) polyglucoside *7 | 4.00 | 3.00 | | | 1.00 | | 2.00 | 2.00 | 1.00 | 0.30 |
| | alkyl (C9-11) glucoside *8 | 4.00 | | 0.05 | 0.30 | 1.00 | 0.20 | 2.00 | | | |
| | polyoxyethylene (16) lauryl ether *9 | 2.00 | 3.00 | | 0.20 | 3.00 | | | 1.00 | | 0.20 |
| (H) | lauric acid amide propylbetaine *10 | | | | | 2.00 | | 0.10 | 2.00 | | 0.30 |
| | cocoamide propylbetaine *11 | 5.00 | 0.20 | | 0.10 | 2.00 | | | 2.00 | | 0.20 |
| | laurylhydroxy sulfobetaine *12 | 5.00 | 0.30 | 0.10 | | 2.00 | 0.10 | | | 4.00 | |
| | propylene glycol | | | 1.00 | 2.00 | | | 5.00 | 3.00 | | 3.00 |
| | dipropylene glycol | | | | | 1.00 | | 2.00 | | | |
| | glycerin | | 7.00 | 5.00 | | 2.00 | 5.00 | | | 5.00 | |
| | sorbitol | 5.00 | 2.00 | | | | 10.00 | | 2.00 | 2.00 | |
| | pH adjuster | q.s. | q.s. | q.s. | q.s. | q.s. | q.s. | q.s. | q.s. | q.s. | q.s. |
| | total | 100 | 100 | 100 | 100 | 100 | 100 | 100 | 100 | 100 | 100 |
| | (B)/(A) weight ratio | 2.00 | 0.01 | 0.25 | 0.33 | 0.40 | 0.05 | 0.50 | 0.20 | 0.09 | 0.25 |
| | (E)/((A) + (B) + (D)) | 0.02 | 0.03 | 0.40 | 0.30 | 0.01 | 0.01 | 0.10 | 0.01 | 0.03 | 0.09 |
| | pH (20 times dilution) | 9.0 | 7.1 | 6.0 | 5.7 | 8.9 | 7.2 | 5.9 | 5.8 | 9.1 | 6.1 |

*1: manufactured by Kao Corporation, effective component of AKYPO 26 (mixture of sodium polyoxyethylene (2.6) lauryl ether carboxylate and sodium polyoxyethylene (2.6) myristyl carboxylate)
*2: manufactured by Kao Corporation, effective component of EMAL 170J
*3: manufactured by Kao Corporation, effective component of EMAL 227
*4: manufactured by Kao Corporation, effective component of KAOAKYPO RLM-45NV
*5: manufactured by Ajinomoto Co., Inc., effective component of AMILITE GCK-11
*6: manufactured by Kao Corporation, effective component of EMANON 3201MH-V
*7: manufactured by Kao Corporation, effective component of AG-124
*8: manufactured by Kao Corporation, effective component of AG-10LK
*9: manufactured by Kao Corporation, effective component of EMULGEN 116
*10: manufactured by Kao Corporation, effective component of AMPHITOL 20AB
*11: manufactured by Kao Corporation, effective component of AMPHITOL 55AB
*12: manufactured by Kao Corporation, effective component of AMPHITOL 20HD

The invention claimed is:

1. A cleansing composition, comprising components (A), (B), and (C):
   (A) from 1 to 20% by weight of a polyoxyethylene alkyl ether carboxylate having an average addition mole number of the polyoxyethylene of 3.5 or less and a number of carbons in the alkyl group of from 10 to 18,
   (B) from 0.02 to 10% by weight of cationized hydroxypropyl cellulose, and
   (C) water,
   wherein the cationized hydroxypropyl cellulose is of formula (1):

$$\left(\begin{array}{c}OR^1\\R^3O\diagdown\diagup O\diagdown\\OR^2\end{array}\right)_n \quad (1)$$

each of $R^1$, $R^2$, and $R^3$ is independently a group having a cationized ethyleneoxy group and a propyleneoxy group of formula (2) or (3):

$$-\left(CH(Y^1)-CH(Y^2)-O\right)_p-(PO)_q-H \quad (2)$$

$$-(PO)_q-\left(CH(Y^1)-CH(Y^2)-O\right)_p-H, \quad (3)$$

n, which is an average polymerization degree of anhydroglucose, is from 20 to 5000,
   an average mole number of the cationized ethyleneoxy group present in a molecule of the cationized hydroxypropyl cellulose per mole of anhydroglucose units is from 0.01 to 3,
   an average mole number of the propyleneoxy group present in a molecule of the cationized hydroxypropyl cellulose per mole of anhydroglucose units is from 0.01 to 5,
   or
   wherein in each of formula (2) and formula (3), one of $Y^1$ and $Y^2$ is a hydrogen atom and the other is a cationic group of formula (4):

$$-\left[CH_2-N^+(R^4)(R^5)(R^6)\right]X^-, \quad (4)$$

in each of formula (2) and formula (3), PO is a propyleneoxy group,
   p, a number of the cationized ethyleneoxy group (—CH($Y^1$)—CH($Y^2$)—O—) in formula (2) or (3), is 0 or 1,
   q, a number of the propyleneoxy group (—PO—) in formula (2) or (3), is from 0 to 4
   when neither p nor q is 0, cationized ethyleneoxy groups and propyleneoxy groups may be arranged in any order,
   when p is 1 and q is 2 or higher, cationized ethyleneoxy groups and propyleneoxy groups may be arranged in blocks or randomly,
   in formula (4), each of $R^4$, $R^5$ and $R^6$ is independently a linear or branched alkyl group having from 1 to 3 carbon atoms, and
   $X^-$ is an anionic group.

2. The cleansing composition according to claim 1, wherein the weight ratio between the components (A) and (B), (B)/(A), is from 0.01 to 2.

3. The cleansing composition according to claim 1, further comprising (D) an anionic surfactant other than the component (A).

4. The cleansing composition according to claim 1, further comprising (E) a salt.

5. The cleansing composition according to claim 1, further comprising (F) long chain fatty acid glycol ester represented by the following formula,

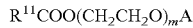

$$R^{11}COO(CH_2CH_2O)_mA$$

wherein $R^{11}$ represents an alkyl group or an alkenyl group having from 11 to 21 carbon atoms, A represents a hydrogen atom or $COR^{12}$ in which $R^{12}$ represents an alkyl group or an alkenyl group having from 11 to 21 carbon atoms, and m represents a number of from 1 to 3.

6. The cleansing composition according to claim 1, further comprising at least one member selected from (G) an alkyl polyglycoside-based non-ionic surfactant and a polyoxyethylene alkyl ether-based non-ionic surfactant.

7. The cleansing composition according to claim 4, wherein the weight ratio between components (A), (B), (D), and (E), (E)/((A)+(B)+(D)), is from 0.02 to 0.4.

8. The cleansing composition according to claim 3, wherein the anionic surfactant as component (D) is at least one member selected from polyoxyalkylene alkyl ether sulfate, fatty acid salt, N-acylamino acid salt, and N-acylalkyl taurine salt.

9. The cleansing composition according to claim 1, wherein component (A), as a salt, is present in an amount of from 1.5 to 11% by weight in the total composition.

10. The cleansing composition according to claim 1, wherein component (B) is present in an amount of from 0.2 to 2% by weight in the total composition.

11. The cleansing composition according to claim 3, wherein component (D) is present in an amount of from 1 to 30% by weight in the total composition.

12. The cleansing composition according to claim 4, wherein component (E) is present in an amount of from 0.1 to 6% by weight in the total composition.

13. The cleansing composition according to claim 5, wherein component (F) is present in an amount of from 0.5 to 3% by weight in the total composition.

14. The cleansing composition according to claim 6, wherein component (G) is present in an amount of from 0.05 to 10% by weight in the total composition.

15. A method for cleansing skin, comprising applying the cleansing composition according to claim 1 on a body skin part for cleansing, followed by rinsing.

* * * * *